United States Patent
Bene et al.

(10) Patent No.: US 6,325,774 B1
(45) Date of Patent: *Dec. 4, 2001

(54) DIALYSIS APPARATUS FOR INDEPENDENTLY CONTROLLING THE CONCENTRATION OF AT LEAST TWO IONIC SUBSTANCES INSIDE A PATIENT'S BODY

(75) Inventors: Bernard Bene, Irigny; Jacques Burtin, Feyzin, both of (FR)

(73) Assignee: Hospal Industrie (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/137,410

(22) Filed: Aug. 20, 1998

(30) Foreign Application Priority Data

Aug. 21, 1997 (FR) .................................................. 97 10670

(51) Int. Cl.[7] .......................... A61M 37/00; A61M 31/00; B01D 11/00; C02F 1/44; C02F 1/00
(52) U.S. Cl. .......................... 604/4.01; 604/5.04; 604/65; 604/66; 210/646; 210/96.2; 210/321.71; 210/739
(58) Field of Search ................................... 604/27, 4, 19, 604/21, 28, 29, 30, 31, 48, 500, 502, 503, 504, 505, 506, 507, 508, 93, 4.01, 5.01, 5.02, 5.04, 6.09, 6.11, 65–67; 210/739, 645, 646, 85, 87, 96.1, 103, 137, 321.65, 321.71, 929, 92.99; 128/692

(56) References Cited

U.S. PATENT DOCUMENTS

| | | |
|---|---|---|
| 4,923,613 | 5/1990 | Chevallet . |
| 5,178,763 | 1/1993 | Delauney . |
| 5,346,472 | 9/1994 | Keshaviah et al. . |
| 5,366,630 | 11/1994 | Chevallet . |
| 5,470,483 | 11/1995 | Bene et al. . |
| 5,567,320 | 10/1996 | Goux et al. . |
| 5,578,223 | * 11/1996 | Bene et al. . |
| 5,744,031 | * 4/1998 | Bene . |
| 5,902,476 | * 5/1999 | Twardowski ............... 210/143 |
| 5,938,938 | 8/1999 | Bosetto et al. . |
| 6,066,261 | * 5/2000 | Spickermann ............... 210/739 |
| 6,123,847 | * 6/2000 | Bene . |

FOREIGN PATENT DOCUMENTS

| | | |
|---|---|---|
| 41 14 908 | 11/1992 | (DE) . |
| 0 192 588 | 8/1986 | (EP) . |
| 516152 | 12/1992 | (EP) . |
| 0 532 433 | 3/1993 | (EP) . |
| 0 658 352 B1 | 6/1995 | (EP) . |
| 2680975 | 12/1993 | (FR) . |
| 2680976 | 12/1993 | (FR) . |

* cited by examiner

Primary Examiner—Angela D. Sykes
Assistant Examiner—Patricia Bianco
(74) Attorney, Agent, or Firm—Finnegan, Henderson, Farabow, Garrett & Dunner, L.L.P.

(57) ABSTRACT

A dialysis apparatus includes a dialysis liquid circuit for circulating sodium chloride and sodium bicarbonate through a haemodialyser and a circuit for infusing a patient with at least one solution containing at least one ionic substance "A" absent from the dialysis liquid. The substance "A" has a determined concentration (A)sol in the infusion solution. A dialysance detector determines the actual dialysance "D" of the haemodialyser for sodium, and a flow rate detector determines the flow rate Qinf of infusion solution such that the concentration of the substance "A" inside the patient's body tends towards a desired concentration (A)des, as a function of the dialysance "D", the concentration (A)sol of the substance "A" in the infusion solution and the desired concentration (A)des, A regulator regulates the flow rate of infusion solution, and a controller drives the regulator to control the flow rate of the infusion solution such that this flow rate is substantially equal to the determined flow rate Qinf.

11 Claims, 1 Drawing Sheet

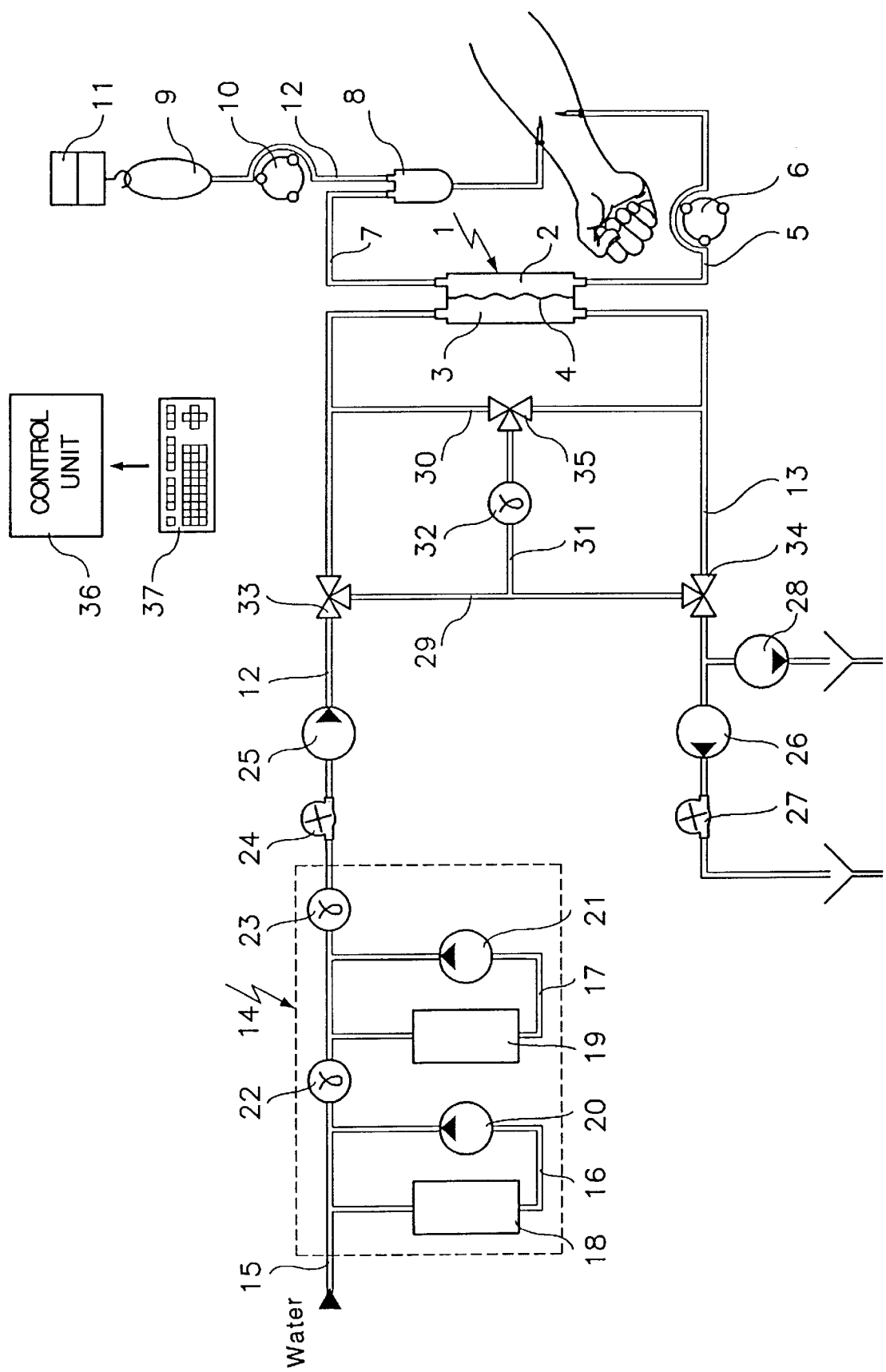

DIALYSIS APPARATUS FOR INDEPENDENTLY CONTROLLING THE CONCENTRATION OF AT LEAST TWO IONIC SUBSTANCES INSIDE A PATIENT'S BODY

BACKGROUND OF THE INVENTION

Field of the Invention

The present invention relates to a dialysis apparatus for independently controlling the concentration of at least two ionic substances inside a patient's body.

The kidneys fulfill many functions, including the removal of water, the excretion of catabolites (or waste from the metabolism, for example urea and creatinine), the regulation of the concentration of the electrolytes in the blood (sodium, potassium, magnesium, calcium, bicarbonates, phosphates, chlorides) and the regulation of the acid/base equilibrium within the body, which is obtained in particular by the removal of weak acids (phosphates, monosodium acids) and by the production of ammonium salts.

In individuals who have lost the use of their kidneys, since these excretion and regulation mechanisms no longer work, the body accumulates water and waste from the metabolism and exhibits an excess of electrolytes (in particular sodium), as well as, in general, acidosis, the pH of the blood plasma shifting towards 7 (the blood pH normally varies within narrow limits of between 7.35 and 7.45).

In order to overcome renal dysfunction, resort is conventionally made to a blood treatment involving extracorporeal circulation through an exchanger having a semipermeable membrane (haemodialyser) in which the patient's blood is circulated on one side of the membrane and a dialysis liquid, comprising the main electrolytes of the blood in concentrations close to those in the blood of a healthy subject, is circulated on the other side. Through the effect of the physical phenomenon referred to as dialysis, the molecules migrate from the liquid where their concentration is higher to the liquid where their concentration is lower.

In conventional dialysis apparatus, the dialysis liquid is prepared by metered mixing of water and two concentrated solutions, the first concentrated solution containing sodium chloride and sodium bicarbonate, and the second concentrated solution containing calcium chloride, potassium chloride and magnesium chloride as well as acetic acid. The function of the acetic acid is to limit the formation of calcium carbonate and magnesium carbonate precipitates which form undesirable deposits in the hydraulic circuit of the dialysis apparatus.

This conventional way of preparing a dialysis liquid has several drawbacks:

- the respective concentrations of the various ionic substances involved in the composition of the dialysis liquid cannot be regulated independently of one another, even though this would be desirable at least for sodium, potassium and bicarbonate;
- for physiological reasons, the acetic acid concentration in the dialysis liquid is necessarily limited, so that carbonated deposits are formed in the hydraulic circuit of the dialysis apparatus. Dialysis apparatus therefore need to be regularly descaled, which places a further burden on their maintenance;
- the presence of acetic acid in the second solution causes corrosion of the connection and pumping means used for transferring the concentrated solution from the reservoir where it is contained to the mixing zone of the apparatus, where it is diluted in the solution obtained by metered mixing of water and the first solution;
- use of a dialysis liquid having a pH less than that of blood at the time when certain types of haemodialysers are started up, that is to say at the time when the dialysis liquid compartment of these haemodialysers is filled with dialysis liquid and the blood compartment is filled with diluted blood, seems to be one of the cofactors of certain hypersensitivity reactions.

Document EP 0 192 588 describes a dialysis apparatus comprising:

- means for circulating a dialysis liquid which contains sodium bicarbonate and is free of calcium and magnesium,
- means for infusing the patient with an infusion solution containing at least calcium and magnesium.

With this apparatus, since the ionic substances (bicarbonate, calcium, magnesium) which can form precipitates when they are combined, are separated, it is not necessary to involve acetic acid in the composition of the dialysis liquid. As described, however, this apparatus cannot be used because it does not comprise means for regulating the infusion flow rate which, in particular, would take into account the diffusive transport of calcium and magnesium through the membrane of the dialyser, from the patient's blood to the dialysis liquid. Now, for safety reasons, it is not envisageable to infuse a patient with a concentrated calcium solution without being able to regulate the infusion flow rate accurately so that there is neither an excess or deficit of this ionic substance within the patient's body.

SUMMARY OF THE INVENTION

The object of the invention is to provide a dialysis apparatus which makes it possible to regulate accurately the flow rate of an infusion liquid containing an ionic substance with a view to making the concentration of this substance inside the patient's body tend towards a desired concentration. More broadly, the object of the invention is to provide a dialysis apparatus which makes it possible to control separately the concentration of at least two ionic substances inside a patient's body by means of a dialysis liquid and an infusion liquid.

This object is achieved by means of dialysis apparatus comprising:

- means for circulating a dialysis liquid containing sodium chloride and sodium bicarbonate through a haemodialyser;
- means for infusing a patient with at least one solution containing at least one ionic substance A (calcium, magnesium, potassium) absent from the dialysis liquid, the substance A having a determined concentration $[A]sol$ in the infusion solution;
- means for determining the actual dialysance D of the haemodialyser for sodium;
- means for determining a flow rate $Qinf$ of infusion solution such that the concentration of the substance A inside the patient's body tends towards a desired concentration $[A]des$, as a function of the dialysance D, of the concentration $[A]sol$ of the substance A in the infusion solution, and of the desired concentration $[A]des$;
- regulating means for regulating the flow rate of infusion solution;
- control means for driving the means for regulating the flow rate of the infusion solution such that this flow rate is substantially equal to the determined flow rate $Qinf$.

In the dialysis apparatus according to the invention, since the dialysis liquid is free of calcium, magnesium and, optionally, potassium, these substances which are present in the blood migrate by diffusion from the blood to the dialysis liquid in the course of the dialysis session. It is in order to compensate for these diffusive losses that provision is made to infuse the patient with a solution containing these substances. The difficulty resides in the fact that these diffusive losses can vary in the course of a dialysis session lasting several hours, and in the fact that an excess or deficit of potassium, calcium and magnesium in the patient's blood can lead to serious disorders, in particular cardiac disorders. By virtue of the invention, this difficulty is overcome since the flow rate of the infusion is slaved to the actual dialysance of the treatment system.

Moreover, further to remedying the drawbacks of conventional dialysis apparatus mentioned above, the apparatus according to the invention also has the following advantage: provided that the infusion liquid is injected directly into the patient or, downstream of the haemodialyser, into the extracorporeal blood circulation circuit connecting the patient to the haemodialyser, the ionic calcium in the blood migrates by diffusion into the dialysis liquid since the latter is free of calcium. Now, ionic calcium is involved in the sequence of reactions constituting the coagulation process of blood. The extensive calcium depletion of the blood in the haemodialyser therefore partially inhibits the coagulation process, which makes it possible to reduce the amount of anticoagulant usually injected into the extracorporeal blood circulation circuit to prevent blood from coagulating in it.

According to one characteristic of the invention, the means for determining the infusion flow rate Qinf comprise calculation means for calculating the infusion flow rate Qinf according to the formula:

$$Qinf = Cl \times [A]des/[A]sol - [A]des$$

where Cl is the clearance of the haemodialyser for the substance A, extrapolated on the basis of the dialysance D for sodium.

According to another characteristic of the invention, the infusion solution contains sodium at a determined concentration [Na+]sol. In this case, the apparatus furthermore includes:

means for preparing the dialysis liquid, comprising means for regulating the sodium concentration of the dialysis liquid;

means for determining the sodium concentration [Na+] dial of the dialysis liquid such that the concentration inside the patient's body tends towards a desired sodium concentration [Na+]des, as a function of the dialysance D, of the flow rate of the infusion liquid Qinf, of the sodium concentration [Na+]sol of the infusion solution, and of the desired sodium concentration [Na+]des;

control means for driving the means for regulating the sodium concentration of the dialysis liquid such that this concentration is equal to the determined concentration [Na+]dial.

According to one characteristic of the invention, the means for determining the sodium concentration [Na+]dial of the dialysis liquid comprise calculation means for calculating this concentration according to the formula:

$$[Na+]dial = \frac{Qinf}{D}([Na+]des - [Na+]sol) + [Na+]des$$

Other characteristics and advantages of the invention will become more clearly apparent on reading the following description. Reference will be made to the single appended FIGURE, which schematically represents a haemodialysis system according to the invention.

BRIEF DESCRIPTION OF THE DRAWINGS

The haemodialysis system represented in the FIGURE comprises a haemodialyser 1 having two compartments 2, 3 separated by a semipermeable membrane 4. A first compartment 2 has an inlet connected to a blood withdrawal line 5, in which a circulation pump 6 is arranged, and an outlet connected to a blood return line 7 in which a bubble trap 8 is inserted.

DESCRIPTION OF A PREFERRED EMBODIMENT

An infusion device, comprising a pump 10 and a balance 11, is provided for injecting the contents of an infusion liquid bag 9 into the bubble trap 8. The bag 9 is suspended from the balance 11 and is connected to the bubble trap 8 by a line 12 in which the infusion pump 10 is arranged. The balance 11 is used to drive the pump 10 such that the flow rate of the infusion liquid is equal to a target flow rate.

The second compartment 3 of the haemodialyser 1 has an inlet connected to a feed line 12 for fresh dialysis liquid, and an outlet connected to a discharge line 13 for spent liquid (dialysis liquid and ultrafiltrate).

The feed line 12 connects the haemodialyser 1 to a device 14 for preparing dialysis liquid, comprising a main line 15 to which two secondary branch lines 16, 17 are connected in series. The upstream end of the main line 15 is intended to be connected to a source of running water. Each secondary line 16, 17 comprises connection means for fitting a cartridge 18, 19 containing a salt in granular form. A pump 20, 21 is arranged in each secondary line 16, 17 downstream of the corresponding cartridge 18, 19 in order to circulate the liquid from the main line through it. Each pump 20, 21 is driven on the basis of comparison between 1) a target conductivity value for the mixture of liquids formed where the main line 15 joins the downstream end of the secondary line 16, 17 and 2) the value of the conductivity of this mixture measured by means of a conductivity probe 22, 23 arranged in the main line 15 immediately downstream of the junction between the main line 15 and the downstream end of the secondary line 16, 17.

The feed line 12 forms an extension of the main line 15 of the device 14 for preparing dialysis liquid. Arranged in this feed line, in the direction in which the liquid circulates, there are a first flow meter 24 and a first circulation pump 25.

The downstream end of the discharge line 13 for spent liquid is intended to be connected to the drain. Arranged in this line, in the direction in which the liquid circulates, there are a second circulation pump 26 and a second flow meter 27. An extraction pump 28 is connected to the discharge line 13, upstream of the second circulation pump 26. The extraction pump 28 is driven in such a way that its delivery rate is equal to a target value for the ultrafiltration rate in the haemodialyser 1.

The feed line 12 and the discharge line 13 are connected by first and second branch lines 29, 30, which are connected together by a junction line 31 in which a conductivity probe 32 is arranged. These branch 29, 30 and junction 31 lines and the conductivity probe 32 form a device for measuring the conductivity of the fresh and spent dialysis liquid which is used, as will be explained below, to determine the actual dialysance (or clearance) of the system for sodium or another substance of similar molecular weight. The first branch line 29 is connected to the feed line 12, downstream of the first circulation pump 25, via a first three-way valve 33, and is connected to the discharge line 13, upstream of the second circulation pump 26, via a second three-way valve 34. The second branch line 30 and the junction line 31 are connected via a third three-way valve 35.

The haemodialysis system represented in FIG. 1 also comprises a calculation and control unit 36. This unit is connected to a user interface (alphanumeric keyboard) 37 through which it receives instructions, such as various target values. It furthermore receives the information output by the measuring instruments of the system, for example the flow meters 24, 27, the conductivity probes 22, 23, 32 and the balance 11. On the basis of the instructions received and the operating modes and algorithms which have been programmed, it drives the active components of the system, such as the pumps 6, 10, 20, 21, 25, 26, 28 and the valves 33, 34, 35.

In the embodiment of the invention which is represented in the FIGURE, the cartridge 18 contains only sodium bicarbonate;

the cartridge 19 contains only sodium chloride; and the infusion liquid bag 9 contains a solution of calcium, magnesium and potassium chloride. The bag 9 optionally also contains sodium.

The haemodialysis apparatus which has just been described operates as follows.

Via the user interface 37, an operator communicates target values corresponding to the various parameters of the treatment (prescription) to the control unit 36, namely the flow rate of blood Qb, the flow rate of the dialysis liquid Qd, the total weight loss WL (amount of plasma fluid to be withdrawn from the patient by ultrafiltration), the total duration T of the session, the bicarbonate concentration [HCO3⁻]dial of the dialysis liquid (which should make it possible for the bicarbonate concentration inside the patient's body to tend towards a desired concentration [HCO3⁻]des), the sodium concentration [Na⁺]dial of the dialysis liquid (which should make it possible for the sodium concentration within the patient's body to tend towards a desired concentration [Na+]des), the potassium concentration [K⁺]sol of the infusion solution, and the potassium concentration [K⁺]des to which the concentration inside the patient's body should tend. After a sodium bicarbonate cartridge 18 and a sodium chloride cartridge 19 have been connected to the corresponding lines 16, 17 of the device 14 for preparing dialysis liquid, the dialysis liquid circuit is filled with dialysis liquid. In order to do this, the main line 15 is connected to a source of running water and the pumps 20, 21, 25, 26 are turned on. The pumps 20 and 21 are regulated by the control unit 36 such that the bicarbonate concentration and the sodium concentration of the dialysis liquid are equal to the corresponding target values [HCO3⁻]dial and [Na⁺]dial. The pumps 25, 26 for circulating dialysis liquid are regulated by the control unit 36 such that the delivery rate of the pump 25 located upstream of the haemodialyser 1 is equal to the target flow rate Qd (for example 500 ml/min) and the delivery rate of the pump 26 located downstream of the haemodialyser 1 is such that the flow rates measured by the flow meters 24, 27 are equal. The three-way valves 33, 34, 35 of the device for measuring the conductivity of the dialysis liquid are arranged such that the conductivity probe 32 is normally exposed to fresh dialysis liquid (the path of the dialysis liquid successively following the lines 12, 29, 31, 30, 12 and 13). In order to rinse and initially fill all the lines for fresh dialysis liquid the valves 33, 34 and 35 are turned at least once so that the conductivity probe 32 is exposed to the liquid leaving the haemodialyser (the path of the dialysis liquid successively following the lines 12, 13, 30, 31, 29 and 13).

At the same time as the dialysis liquid circuit is filled with the dialysis liquid according to the prescription, the extracorporeal blood circulation circuit is rinsed and filled with sterile saline solution.

When the dialysis liquid circuit and the blood circuit have been primed, the blood circuit is connected to the patient and the treatment proper can begin: the pumps 20, 21 of the device 14 for preparing dialysis liquid, as well as the pumps 25, 26 for circulating the dialysis liquid continue to operate as when the circuit is being primed, while the blood pump 6, the extraction pump 28 and the infusion pump 10 are turned on. The blood pump 6 is regulated to the target flow rate Qb (for example 200 ml/min) and the extraction pump 28 is regulated to a flow rate QUF calculated by the control unit 36, on the basis of the target values for the total weight loss WL and the total duration of the treatment T.

According to the invention, the infusion pump 10 is regulated to a flow rate Qinf calculated by the control unit 36 on the basis of the following formula:

$$Qinf = Cl \times \frac{[K+]des}{[K+]sol - [K+]des} \quad (1)$$

where Cl is the clearance of the haemodialyser 1 for potassium. The infusion pump 10 is regulated accurately by the control unit 6 on the basis of the information supplied by the balance 11. The actual clearance Cl for potassium is obtained by extrapolation from the actual dialysance for sodium D, which is determined by implementing the following process, in which the successive steps are controlled by the control unit 36. With the three-way valves 33, 34, 35 arranged in such a way that the fresh dialysis liquid irrigates the conductivity probe 32, the conductivity Cd1in of the fresh dialysis liquid corresponding to the prescription is measured and stored. The three valves 33, 34, 35 are then turned so that the conductivity probe 32 is irrigated by the spent liquid, and the conductivity Cd1out of this liquid is measured and stored. The delivery rate of the pump 21 for concentrated sodium chloride solution is then modified (increased or decreased) so that the conductivity of the dialysis liquid circulated is slightly different from the conductivity of the dialysis liquid of the prescription. For example, the conductivity of the second dialysis liquid is regulated so as to be 1 mS/cm greater or less than the conductivity of the first dialysis liquid (which is generally of the order of 14 mS/cm). As before, the conductivity Cd2in of the second dialysis liquid upstream of the haemodialyser is measured and stored, after which the three-way valves 33, 34, 35 are again turned so that the conductivity probe 32 is irrigated by the spent liquid, and the conductivity Cd2out of the spent liquid is measured and stored.

The dialysance for sodium can then be calculated by applying the following formula:

$$D = Qd \times \frac{(Cd1out - Cd1in) - (Cd2out - Cd2in)}{Cd2in - Cd1in} \quad (2)$$

where Qd is the flow rate of the dialysis liquid.

Another process for calculating the dialysance D on the basis of measurements taken with two dialysis liquids having different conductivities is described in Patent Application EP 0 658 352.

In the particular case of treatment by continuous haemodialysis, in which the flow rate of the dialysis liquid is very much less than the blood flow rate (of the order of three times), the flow rate Qinf of the infusion solution can be calculated at any time by applying the formula:

$$Qinf = \frac{[K+]des}{[K+]sol} \times Qout \quad (3)$$

where Qout is the flow rate of spent liquid leaving the haemodialyser, which is equal to the sum of the flow rate of fresh dialysis liquid, as determined by the circulation pumps 25, 26, and the flow rate of the extraction pump 28.

EXAMPLE 1

The target to be achieved, in terms of potassium concentration [K+]des inside the body is 2 mEq/l.

A blood-isotonic infusion liquid is chosen, in which the relative proportions of the ions are equal to the desired relative proportions for the same ions inside the patient's body. The infusion liquid may, for example, have the following composition:

[K+]=42 mEq/l

[Mg++]=31.3 mEq/l

[Ca++]=73.5 mEq/l

[Cl−]=147 mEq/l

If the actual dialysance D is, for example, 150 ml/min, the infusion flow rate which the control unit calculates by means of formula (1) and imposes on the infusion pump 10 is 0.45 l/h.

According to the invention, the intention is to be able to use the dialysis apparatus that has just been described to carry out a haemodiafiltration treatment with a high flow rate of infusion liquid (more than 1 l/h). In this case, it is not possible to use a blood-isotonic infusion liquid containing only potassium, calcium and magnesium chloride (like the one described in Example 1) because this would lead to the patient becoming overloaded with these ionic substances.

It is therefore necessary to envisage the use of a substitute liquid in which the potassium, calcium and magnesium concentrations are lower and which furthermore contains sodium so as to remain isotonic with blood. The problem then encountered is of regulating the sodium concentration of the dialysis liquid while taking account of the variable-rate infusion of an infusion liquid containing sodium, so that the patient's body tends towards a desired sodium concentration [Na+]des.

According to the invention, the delivery rate of the pump 21 for concentrated sodium chloride solution is adjusted continuously so that the sodium concentration [Na+]dial of the dialysis liquid, as measured by the conductivity probe 23, can make the sodium concentration inside the patient's body tend towards a desired value [Na+]des. The sodium concentration [Na+]dial of the dialysis liquid is calculated by the calculation unit 36 on the basis of the dialysance D of the haemodialyser for sodium, the infusion flow rate Qinf, the sodium concentration [Na+]sol of the infusion solution, and the desired sodium concentration [Na+]des towards which the patient's body should tend. It can be calculated by applying the following formula:

$$[Na+]dial = \frac{Qinf}{D}([Na+]des - [Na+]sol) + [Na+]des \quad (4)$$

EXAMPLE 2

The target to be achieved, in terms of the potassium concentration [K+]des inside the body is 2 mEq/l.

The target to be achieved, in terms of the sodium concentration [Na+]des inside the body is 140 mEq/l.

The desired infusion flow rate is about 1 l/h.

A blood-isotonic infusion liquid is chosen, in which the relative proportions of the ions are equal to the desired relative proportions for the same ions inside the patient's body. The infusion liquid may, for example, have the following composition:

[K+]=20 mEq/l

[Mg++]15 mEq/l

[Ca++]=35 mEq/l

[Na+]=77 mEq/l

[Cl−]=147 mEq/l

If the actual dialysance D is, for example, 150 ml/min, the infusion flow rate which the control unit 36 calculates by means of formula (1) and imposes on the infusion pump 10 is 1 l/h. Furthermore, the delivery rate which the control unit 36 imposes on the pump 21 for concentrated sodium chloride solution is such that the sodium concentration [Na+]dial of the dialysis liquid is equal to 154.8 mEq/l (concentration calculated by means of formula (4)).

EXAMPLE 3

The target to be achieved, in terms of the potassium concentration [K+]des inside the body is 2 mEq/l.

The target to be achieved, in terms of the sodium concentration [Na+]des inside the body is 140 mEq/l.

The desired infusion flow rate is about 2 l/h.

A blood-isotonic infusion liquid is chosen, in which the relative proportions of the ions are equal to the desired relative proportions for the same ions inside the patient's body. The infusion liquid may, for example, have the following composition:

[K+]=10 mEq/l

[Mg++]=7.5 mEq/l

[Ca++]=17.5 mEq/l

[Na+]=112 mEq/l

[Cl−]=147 mEq/l

If the actual dialysance D is, for example, 150 ml/min, the infusion flow rate which the control unit 36 calculates by means of formula (1) and imposes on the infusion pump 10 is 2.25 l/h. Furthermore, the delivery rate which the control unit 36 imposes on the pump 21 for concentrated sodium chloride solution is such that the sodium concentration [Na+]dial of the dialysis liquid is equal to 147 mEq/l (concentration calculated by means of formula (4)).

EXAMPLE 4

The target to be achieved, in terms of the potassium concentration [K$^+$]des inside the body is 2 mEq/l.

The target to be achieved, in terms of the sodium concentration [Na$^+$]des inside the body is 140 mEq/l.

The desired infusion flow rate is about 4.5 l/h.

A blood-isotonic infusion liquid is chosen, in which the relative proportions of the ions are equal to the desired relative proportions for the same ions inside the patient's body. The infusion liquid may, for example, have the following composition:

[K$^+$]=6 mEq/l

[Mg$^{++}$]=4.5 mEq/l

[Ca$^{++}$]=10.5 mEq/l

[Na$^+$]=126 mEq/l

[Cl$^-$]=147 mEq/l

If the actual dialysance D is, for example, 150 ml/min, the infusion flow rate which the control unit 36 imposes on the infusion pump 10 is 4.5 l/h. Furthermore, the delivery rate which the control unit 36 imposes on the pump 21 for concentrated sodium chloride solution is such that the sodium concentration [Na+]dial of the dialysis liquid is equal to 147 mEq/l (concentration calculated by means of formula (4)).

In the above examples, the target to be achieved was defined in terms of the potassium concentration [K$^+$]des inside the body. It is obvious that, when calcium or magnesium are considered as the critical substance for a certain patient, the infusion pump 10 will be regulated on the basis of a target defined in terms of the desired calcium [Ca$^{++}$]des or magnesium [Mg$^{++}$]des concentration inside the patient's body.

Variants may be made to the invention which has just been described.

In the embodiment which was described above, only one of the ionic substances contained in the infusion liquid can be metered accurately inside the body. This is due to the fact that only one infusion solution is used, containing all the ionic substances to be infused. If it is desired to meter several ionic substances accurately, it is sufficient to use several infusion liquid bags, each containing a single ionic substance to be metered, and to provide a corresponding number of infusion means (balance and pump). It is also possible to use only a single balance, from which the various bags are suspended, and only a single pump which is associated with distribution means for in turn connecting each bag and the extracorporeal blood circulation circuit according to a determined time sequence.

Instead of a single conductivity probe, to which the fresh dialysis liquid and the spent liquid are successively applied, the dialysis liquid circuit may be equipped with two conductivity probes which are arranged in the dialysis liquid circuit, respectively upstream and downstream of the haemodialyser. The dialysis liquid circuit may also include only one conductivity probe, arranged downstream of the haemodialyser, in which case the two target conductivity values used for driving the concentrate pump 21 in order to prepare the first and second dialysis liquids are substituted in the formula indicated above for the conductivity values measured upstream of the haemodialyser.

What is claimed is:

1. Dialysis apparatus comprising:

means for circulating a dialysis liquid containing sodium chloride and sodium bicarbonate through a haemodialyser;

means for infusing a patient with at least one solution containing at least one ionic substance A absent from the dialysis liquid, the substance A having a determined concentration (A)sol in the infusion solution;

means for measuring the conductivity of the dialysis liquid upstream and downstream of the haemodialyser;

means for calculating an actual dialysance D using at least two conductivity values (Cd1in, Cd1out, Cd2in, Cd2out) measured respectively upstream and downstream of the haemodialyser in at least two successively prepared dialysis liquids and using the formula:

$$D = \frac{Qd \times (Cd1out) - Cd1in) - (Cd2out - Cd2in)}{Cd2in - Cd1in}$$

where Qd is the flow rate of dialysis liquid;

means for determining a flow rate Qinf of infusion solution such that the concentration of the substance A inside the patients body tends towards a desired concentration (A)des, as a function of the dialysance D, of the concentration (A)sol of the substance A in the infusion solution, and of the desired concentration (A)des;

regulating means for regulating the flow rate of infusion solution; and control means for driving the means for regulating the flow rate of the infusion solution such that this flow rate is substantially equal to the determined flow rate Qinf.

2. Dialysis apparatus according to claim 1, wherein the means for determining the infusion flow rate Qinf comprise calculation means for calculating the infusion flow rate Qinf according to the formula:

$$Qinf = Cl \times \frac{(A)des}{(A)sol - (A)des}$$

where Cl is the clearance of the haemodialyser for the substance A, extrapolated on the basis of the dialysance D for sodium.

3. Dialysis apparatus according to claim 1, wherein the infusion solution contains sodium at a determined concentration (Na+)sol.

4. Dialysis apparatus according to claim 3, further including:

means for preparing the dialysis liquid, comprising means for regulating the sodium concentration of the dialysis liquid;

means for determining the sodium concentration (Na+)dial of the dialysis liquid such that the concentration inside the patient's body tends towards a desired sodium concentration (Na+)des, as a function of the dialysance D, of the flow rate of the infusion liquid Qinf, of the sodium concentration (Na+)sol of the infusion solution, and of the desired sodium concentration (Na+)des; and control means for driving the means for regulating the sodium concentration of the dialysis liquid such that this concentration is equal to the determined concentration (Na+)dial.

5. Apparatus according to claim 4, wherein the means for determining the sodium concentration (Na+)dial of the dialysis liquid comprises calculation means for calculating this concentration according to the formula:

$$(Na+)dial = \frac{Qinf}{D}((Na+)des - (Na+)sol) + (Na+)des$$

6. Apparatus according to claim 1, further including means for preparing a dialysis liquid from a first concentrated solution of sodium chloride and a second concentrated solution of sodium bicarbonate, these preparation means comprising means for regulating the sodium concentration and the bicarbonate concentration of the dialysis liquid independently of one another.

7. Apparatus according to claim 6, the means for preparing dialysis liquid comprise means for producing the first concentrated solution from sodium chloride in powder or granular form.

8. Apparatus according to claim 6, the means for preparing dialysis liquid comprise means for preparing the second concentrated solution from sodium bicarbonate in powder or granular form.

9. Apparatus according to claim 1, wherein the infusion means is designed to be connected to an extracorporeal blood circuit which includes the blood compartment of the haemodialyser, downstream of the haemodialyser.

10. Apparatus according to claim 1, wherein the substance A is selected from calcium, potassium and magnesium.

11. Dialysis apparatus comprising:

means for circulating a dialysis liquid containing sodium chloride and sodium bicarbonate through a haemodialyser;

means for infusing a patient with at least one solution containing at least one ionic substance A absent from the dialysis liquid, the substance A having a determined concentration (A)sol in the infusion solution, wherein the infusion solution contains sodium at a determined concentration (Na+)sol;

means for preparing the dialysis liquid, comprising means for regulating the sodium concentration of the dialysis liquid;

means for determining a sodium concentration (Na+)dial of the dialysis liquid such that a concentration inside a patient's body tends towards a desired sodium concentration (Na+)des, as a function of a dialysance D, a flow rate of the infusion solution Qinf, the sodium concentration (Na+)sol of the infusion solution, and the desired sodium concentration (Na+)des, wherein the means for determining the sodium concentration employs the formula:

$$(Na+)dial = \frac{Qinf}{D}((Na+)des - (Na+)sol) + (Na+)des$$

means for driving the means for regulating the sodium concentration of the dialysis liquid such that this concentration is substantially equal to the determined concentration (Na+)dial;

means for determining an actual dialysance D of the haemodialyser for sodium;

means for determining a flow rate Qinf of infusion solution such that the concentration of the substance A inside the patient's body tends towards a desired concentration (A)des, as a function of the dialysance D, of the concentration (A)sol of the substance A in the infusion solution, and of the desired concentration (A)des;

regulating means for regulating the flow rate of infusion solution; and control means for driving the means for regulating the flow rate of the infusion solution such that this flow rate is substantially equal to the determined flow rate Qinf.

* * * * *

UNITED STATES PATENT AND TRADEMARK OFFICE
CERTIFICATE OF CORRECTION

PATENT NO. : 6,325,774 B1
DATED : December 4, 2001
INVENTOR(S) : Bernard Béné

Page 1 of 1

It is certified that error appears in the above-identified patent and that said Letters Patent is hereby corrected as shown below:

Column 10,
Line 30, "patients" should read -- patient's --.

Column 11,
Line 20, before "the means", insert -- wherein --.
Line 24, before "the means", insert -- wherein --.

Signed and Sealed this

Twenty-third Day of April, 2002

Attest:

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.    : 6,325,774 B1
DATED         : December 4, 2001
INVENTOR(S)   : Bernard Béné

It is certified that error appears in the above-identified patent and that said Letters Patent is hereby corrected as shown below:

Column 3,
Line 37, the equation "Qinf = Cl x [A]des/[A]sol - [A]des" should read $$--\text{Qinf} = \text{Cl} \times \frac{[A]des}{[A]sol - [A]des} --;$$

Column 10,
Lines 23-25, the equation "$D = \frac{Qd \times (Cd1out - Cd1in) - (Cd2out - Cd2in)}{Cd2in - Cd1in}$" should read $$--D = Qd \times \frac{(Cd1out - Cd1in) - (Cd2out - Cd2in)}{Cd2in - Cd1in}--$$

Signed and Sealed this

Twenty-first Day of October, 2003

JAMES E. ROGAN
*Director of the United States Patent and Trademark Office*